United States Patent [19]

Tampa

[11] Patent Number: 4,628,932

[45] Date of Patent: Dec. 16, 1986

[54] KNEE ICE PACK

[76] Inventor: Morris Tampa, P.O. Box 31346, St. Petersburg, Fla. 33733

[21] Appl. No.: 619,129

[22] Filed: Jun. 11, 1984

[51] Int. Cl.$^4$ .............................................. A61F 7/10
[52] U.S. Cl. ................................... 128/402; 128/403; 383/901
[58] Field of Search ............... 128/402, 403, DIG. 15; 62/530; 383/901

[56] References Cited

U.S. PATENT DOCUMENTS

| 1,769,186 | 7/1930 | Morris | 128/402 |
| 1,927,751 | 9/1933 | Mensi | 128/403 X |
| 3,463,161 | 8/1969 | Andrassy | 128/402 |
| 4,055,188 | 10/1977 | Pelton | 128/402 |
| 4,488,552 | 12/1984 | McCann et al. | 128/402 |

Primary Examiner—Anton O. Oechsle
Attorney, Agent, or Firm—Stein, Reese & Prescott

[57] ABSTRACT

A knee ice pack for cooling the affected area of a knee including a body member having left, center and right compartments open along the top portions thereof and adapted to receive ice therein, the center compartment having a through opening intended to be aligned with the patella to preclude the patella from being subjected to the cooling effects of the ice, a closure fastener for permitting opening and closing of the top portions of the compartments to provide access thereto, and a fastener for securing the ice pack to the knee.

3 Claims, 5 Drawing Figures

U.S. Patent     Dec. 16, 1986     4,628,932
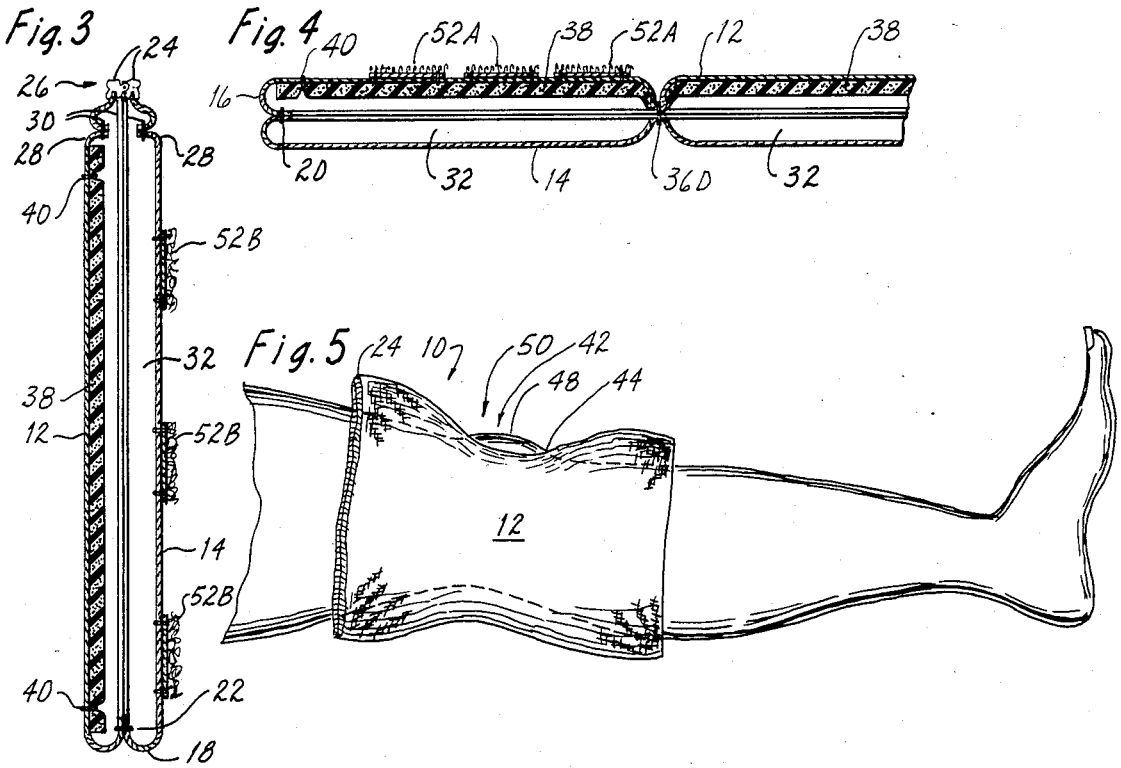

KNEE ICE PACK

BACKGROUND OF THE INVENTION

1. Field of the Invention

This invention relates to devices used in the application of heat or cold to various portions of the appendages of the human body. More particularly, this invention relates to ice packs designed to be fitted about an appendage of the human body to effectuate the application of cold to an affected area such as the knee.

2. Description of the Prior Art

Presently there exist many types of devices designed to be filled with a cold or hot medium and then applied to an affected area of the human body or an animal such as a horse. The most basic of such devices consists of a hot water bag in which a bladder is filled with hot water and then applied to the affected area. Another most basic type of these devices include ice packs in which a bladder is filled with ice and then applied to the affected area. The more common forms of such devices consist of generally rectangular bladders having a filling cap at one end or a generally circular bladder with a fill cap at its center. It has long been recognized that one major disadvantage to these types of devices is their inability to be easily secured about the affected area of the appendage so that the person could freely move about without constantly holding the device into position.

With somewhat limited success, various methods have been invented which seek to affix the devices to the affected area of the body. For example, U.S. Pat. No. 3,889,684 discloses a hot and cold pack comprising an encapsulated absorbent pad positioned within a cover. A plurality of fasteners is attached to the edges of the cover allowing the pack to be positioned over a large body portion such as the back, shoulder or stomach or to be applied to other body members such as the ankle, neck or face. U.S. Pat. No. 4,044,773 discloses a similar cold pack which comprises a supply of water encapsulated within a relatively thin polyurethane bladder. After the freezing of the water within the bladder, the resulting thin layer of ice is fragmented into small particles, thereby allowing the pack to be more appropriately fitted about the affected area of the appendage. U.S. Pat. No. 2,949,914 discloses an ice pack for an ankle which basically comprises an ice containing bag which is fitted about the ankle by means of a drawstring. In a similar fashion, U.S. Pat. No. 3,491,761 discloses an ice bag harness including several pockets adapted to receive an ice bag. The harness includes tie strap allowing the harness to be fitted about an appendage and tied.

In addition to the devices disclosed in the foregoing patents, there has also been developed ice packs which function in the conventional manner as an ice pack but also function as a splint to immobilize the appendage to which the ice pack is affixed. For example, U.S. Pat. Nos. 3,548,819 and 3,561,435 disclose an ice pack including an air fillable bladder which functions as a splint.

Therefore, it is an object of this invention to provide an apparatus which overcomes the aforementioned inadequacies of the prior art devices and provides an improvement which is a significant contribution to the advancement of the ice pack art.

Another object of this invention is to provide an ice pack adapted to be filled with ice and then fitted about the knee of a person.

Another object of this invention is to provide an ice pack having a design which, when fitted about the knee of a person, remains in proper position about the knee even while the person is walking or is otherwise mobile.

Another object of this invention is to provide an ice pack having a plurality of individualized compartments for receiving the ice to be used during treatment to assure that the cooling effects of the ice is concentrated to each area of the affected area to be treated.

Another object of this invention is to provide an ice pack having individualized compartments for receiving ice in such a manner that a certain degree of bending motion is allowed while the person is wearing the knee ice pack.

Another object of this invention is to provide a knee ice pack having a recessed area located proximate to the patella area (kneecap) of the knee to prevent the patella area from being subject to the cold treatment while allowing the affected areas of the knee to be treated.

Another object of this invention is to provide a knee ice pack having a cut-out recess to assure that the ice positioned within the individualized compartments will not come in thermal contact with the patella area of the knee.

Another object of this invention is to provide a knee ice pack having an opening at the upper portion thereof to facilitate easy filling of the ice pack with ice.

Another object of this invention is to provide a knee ice pack having an opening at its upward end which includes a zipper.

Another object of this invention is to provide a knee ice pack having individualized compartments which are insulated from the ambient air to concentrate the cooling effects of the ice to the affected area of the knee rather than being lost to the ambient air.

Another object of this invention is to provide a knee ice pack including fastener means which permits the ice pack to be easily fitted about the knee of the injured person.

Another object of this invention is to provide a knee ice pack which can be worn by the injured person for significant periods of time without excessive melting of the ice contained therein due to the ambient environment.

Another object of this invention is to provide a knee ice pack in which the fastener comprises the fastener sold under the trademark "Velcro" to permit the ice pack to be easily positioned about the knee or removed therefrom.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises an ice pack adapted to be affixed about the knee of a person. More particularly, the ice pack of the invention comprises a front and a back sheet of material which are sewn together along their bottom and side edges to form an open-ended, waterproof enclosure. A fastener such as a zipper is affixed to the opened top end of the ice pack to allow the ice pack to be filled with cubed or crushed ice. The interior of the ice pack comprises a plurality of individualized compartments which function to retain the ice in specific areas of the ice pack thereby preventing "bunching" of the ice during use. One area of the ice pack, which would be located proximate to the patella area of the knee, is cut out and sewn together to form a recessed area which assures that the thermal properties of the ice do not adversely affect the patella area of the knee. Finally, fastener strips, such as those sold under the trademark "Velcro" and disclosed in U.S. Pat. Nos. 2,717,437, 3,192,587 and 3,387,341, are vertically and horizontally positioned along the sides of the ice pack to allow the ice pack to be adjustably fitted about the knee of the person.

During use, the individualized compartments of the knee ice pack are filled with ice, preferably crushed. The zipper is then zipped shut. The ice pack is fitted about the knee of the person in such a manner that the cut-out recess is positioned about the knee cap. After pulling to a desired tightness, the fasteners are fastened to securely affix the ice pack about the knee. As the ice melts within one or more of the compartments, the opened end of the ice pack may be unzipped, drained of accumulated fluid from the melted ice and the compartment(s) refilled with a suitable amount of ice.

From the foregoing, it should be appreciated that the ice pack of the invention includes many advantages over the prior art devices disclosed above. Specifically, the ice pack of this invention may be conveniently filled with cubed or crushed ice and then removably affixed about the knee of a person. The compartmentalized feature of the invention assures that the ice will be properly dispersed about the knee. Additionally, should an affected area of the knee need more cooling than another area, the compartment adjacent to such affected area may be filled with additional ice to provide additional cooling effect to that affected area. Since it is usually desirable to prevent cooling of the patella area of the knee, the cut-out recess of the ice pack of the invention assures that such patella area will not be cooled to any adverse degree. However, because of the unique design of the compartment through which the cut-out recess is formed, all areas around the patella area may still be treated.

The adjustable fastener of the ice pack of this invention permits the ice pack to be fitted to children and adults. Specifically, the adjustable fastener allows the ice pack to be positioned about the knee with any degree of tightness. Additionally, the ice pack, through the use of the adjustable fastener, allows the ice pack to be immediately positioned about or removed from the knee of the person. This feature of the invention is of particular benefit to professional athletes who participate in organized sports. Specifically, should an athlete become injured, the attending persons may immediately affix the ice pack about the injured knee of the athlete even while the athlete is still on the field. Obviously, the ability to immediately ice the injured knee will be of significant benefit to the athlete. Likewise, an athlete who has an affected knee may conveniently affix the ice pack about his knee during breaks in the game to minimize inflammation in the knee to the greatest extent possible.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is an outside plan view of the knee ice pack of the invention illustrating the cut-out recess of the ice pack for positioning about the patella area of the knee;

FIG. 2 is a rear plan view of the knee ice pack of the invention;

FIG. 3 is a cross-sectional view of FIG. 1 along lines 3—3 illustrating the manner in which the zipper is affixed to the upper, opened end of the ice pack;

FIG. 4 is a cross-sectional view of FIG. 2 along lines 4—4 partially illustrating the individualized compartments of the ice pack and the manner in which the individualized compartments are insulated from the ambient air; and FIG. 5 is a side plan view of the knee ice pack of the invention affixed about the knee of a leg of a person illustrating the manner in which the patella cut-out recess is fitted about the patella of the knee.

Similar reference characters refer to similar parts throughout the several views of the drawings.

DETAILED DESCRIPTION OF THE PREFERRED EMBODIMENT

The ice pack 10 of the invention comprises a front and back sheets of material 12 and 14 (preferably waterproof) whose side and bottom edges 16 and 18 are turned in with respect to one another and sewn by means of stitching 20 and 22, respectively.

A closure type fastener 24 is affixed to the opened end 26 of the ice pack 10. Preferably, the closure type fastener 24 comprises a conventional zipper having its ribbon edges fastened to the upper edges 28 of the sheets of the material 12 and 14 by means of stitching 30. Obviously, the zipper closure 24 permits access to the interior of the ice pack 10 formed by the sheets of material 12 and 14. Without departing from the spirit and scope of this invention, other types of closures type fasteners 24 may be utilized in substitution of the zipper type closure 24.

The interior 32 formed by the sheets of material 12 and 14 is preferably compartmentalized. Specifically, individual compartments 34A, 34B, 34C, 34D, and 34E may be formed within the interior 32 by simply sewing a seam 36A-D from the bottom edge 18 to the upper edges 28 of the combined sheets of material 12 and 14. It shall be understood that although only five vertically disposed compartments are illustrated, any other variation may be used without departing from the spirit and scope of this invention. For example, the interior 32 of the ice pack 10 may be divided into more than, or less than, five compartments 34. Additionally, without departing from the spirit and scope of this invention, the interior volume of one or more of the compartments 34 may be effectively increased by simply oversizing one or both of the sheets of material 12 and 14 and then gathering the edges thereof during the sewing of the stitched seams 20, 22, and 28 to form a "boxed" compartment 34. For example, compartments 34B and 34D, which correspond to the sides of the knee when the ice pack 10 of the invention is affixed thereto, may be oversized to allow filling with additional ice such that the sides of the knee will receive more cooling than the other areas of the knee.

A sheet of insulative material 38 is affixed to the inside surface of the front sheet of material 12 by means of stitching 40 or the like. Alternatively, the sheet of insulative material 38 may be affixed to the outside surface of the front sheet of material 12. In either case, the sheet of insulative material 38 functions to insulate the ice contained within the interior 32 of the ice pack 10 from the ambient air. This assures that the ice contained within the ice pack 10 will not significantly melt due to exposure to the ambient air but, rather, primarily melt upon absorption of heat from the affected area of the person's knee. Accordingly, the ice pack 10 of the invention, having the insulative material 38 affixed thereto, will significantly increase the wearing time of the ice pack 10 before refilling of the compartments 34 with ice becomes necessary.

The ice pack 10 of the invention further comprises a cut-out recess 42 located within the center compartment 34C. The cut-out recess 42 is preferably circular in design having its peripheral edges 44 sewn together by means of stitching 46. As shown in FIG. 5, the recess 42 is positioned within the center compartment 34C in such a manner to be aligned with the patella area 48 (kneecap) of a person's knee 50. It is apparent that the recess 42 precludes the thermal effect of the ice from adversely affecting the patella 48. Further, it is apparent that the ice is allowed to flow into the areas to the side and the bottom of the recess 42 within the compartment 34C to assure that all areas of the knee 50 other than the patella area 48 is subjected to the cooling effect of the ice.

Adjustable fastener means, generally indicated by the numeral 52, is provided to allow the ice pack 10 of the invention to be easily and adjustably fitted about a person's knee 50. In the specific embodiment illustrated, the fastner means 52 comprises the two-part fastener sold in male and female strips 52A and 52B under the trademark "Velcro". More particularly, the male strips 52A are vertically sewn, parallel to one another, to the front sheet of material 12 at one end of ice pack 10. Correspondingly, the female strips 52B are horizontally sewn, parallel to one another, to the back sheet of material 14 at the other end of the ice pack 10 in mating alignment with the male strips 52A. During use, the ice pack 10 of the invention is simply positioned about the knee 50, with the recess 42 aligned with the patella 48. The one end of the ice pack 10 having the male strips 52A is then simply overlapped with the other end having the female strips 52B. The two strips of the fastners 52 are then joined to securely fasten both ends together about the knee 50. The ice pack 10 may be removed from the knee 50 by simply pulling on the end having the female strips 52B until the same is unfastened from the male strips 52A.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described, What is claimed is:

1. A knee pack for cooling the affected area of a knee with ice without also cooling the patella of the knee, comprising in combination:

a body member having a front sheet of material affixed to a back sheet of material defining an open-ended enclosure open along a top portion thereof, said body member being segmented into a left, center and right compartments each adapted to receive ice therein, said center compartment including a cut-out recess defined by affixed edges of said front and back sheets, said recess being centrally positioned within said center compartment for alignment with the patella of the knee to preclude the patella from being subjected to cooling effects of the ice;

closure fastener means affixed completely across the opened end of said body member to permit opening and closing thereof to gain access to each said compartments, said closure fastener means comprising a zipper; and means for removably fastening said body member about the knee with said cut-out recess being aligned with the patella of the knee, said fastening means comprising male and female strips of fastener material affixed to said left and right compartments, respectively, of said body member to be in mating and transverse engagement with one another when said left and right compartments are overlapped with one another, whereby the knee ice pack is positioned about the knee by first aligning said cut-out recess with the patella of the knee and then overlapping said left and right side compartments to engage said male and female strips of said fastener material such that the cooling effects of the ice contained within said compartments are concentrated along the sides and back of the knee and are substantially precluded from cooling the patella of the knee.

2. The ice pack as set forth in claim 1, wherein said body portion is composed of a waterproof material.

3. The ice pack as set forth in claim 2, further including insulative means affixed to said body portion for insulating ice contained therein from the environment.

* * * * *